(12) United States Patent
Gunderson

(10) Patent No.: US 9,737,427 B2
(45) Date of Patent: *Aug. 22, 2017

(54) MEDICAL DEVICE DELIVERY SYSTEMS

(71) Applicant: BOSTON SCIENTIFIC SCIMED, INC., Maple Grove, MN (US)

(72) Inventor: Richard C. Gunderson, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,061

(22) Filed: Jun. 24, 2015

(65) Prior Publication Data

US 2015/0290008 A1    Oct. 15, 2015

Related U.S. Application Data

(63) Continuation of application No. 11/100,712, filed on Apr. 7, 2005, now Pat. No. 9,066,826, which is a continuation-in-part of application No. 10/822,251, filed on Apr. 9, 2004, now abandoned.

(51) Int. Cl.

| | | |
|---|---|---|
| *A61F 2/06* | (2013.01) | |
| *A61F 2/966* | (2013.01) | |
| *A61F 2/91* | (2013.01) | |
| *A61F 2/95* | (2013.01) | |
| *A61F 2/958* | (2013.01) | |

(52) U.S. Cl.
CPC .............. *A61F 2/966* (2013.01); *A61F 2/91* (2013.01); *A61F 2/95* (2013.01); *A61F 2002/9505* (2013.01); *A61F 2002/9522* (2013.01); *A61F 2002/9583* (2013.01); *A61F 2002/9665* (2013.01); *A61F 2220/0008* (2013.01); *A61F 2220/0016* (2013.01)

(58) Field of Classification Search
CPC .............. A61F 2/966; A61F 2002/9665; A61F 2002/9583; A61F 2220/0008; A61F 2220/0016; A61F 2002/9505; A61F 2002/9522; A61F 2/95; A61F 2/91
See application file for complete search history.

(56) References Cited

U.S. PATENT DOCUMENTS

| | | | |
|---|---|---|---|
| 4,503,569 | A | 3/1985 | Dotter |
| 4,733,665 | A | 3/1988 | Palmaz |
| 4,950,227 | A | 8/1990 | Savin et al. |
| 4,990,151 | A | 2/1991 | Wallstén |
| 5,026,377 | A | 6/1991 | Burton et al. |
| 5,290,295 | A | 3/1994 | Querals et al. |

(Continued)

FOREIGN PATENT DOCUMENTS

| | | |
|---|---|---|
| EP | 0819411 A2 | 1/1998 |
| EP | 1157673 A2 | 11/2001 |

(Continued)

OTHER PUBLICATIONS

Ellis et al. U.S. Appl. No. 08/697,453, filed Aug. 23, 1996.

(Continued)

*Primary Examiner* — Richard Louis
(74) *Attorney, Agent, or Firm* — Seager, Tufte & Wickhem, LLP

(57) ABSTRACT

Medical device delivery systems, and related methods and components, are disclosed.

17 Claims, 6 Drawing Sheets

(56) References Cited

U.S. PATENT DOCUMENTS

| | | | |
|---|---|---|---|
| 5,409,495 A | 4/1995 | Osborn | |
| 5,484,444 A | 1/1996 | Braunschweiler et al. | |
| 5,534,007 A | 7/1996 | St. Germain et al. | |
| 5,645,559 A | 7/1997 | Hachtman et al. | |
| 5,693,066 A | 12/1997 | Rupp et al. | |
| 5,702,418 A | 12/1997 | Ravenscroft | |
| 5,707,376 A | 1/1998 | Kavteladze et al. | |
| 5,709,703 A | 1/1998 | Lukic et al. | |
| 5,725,549 A | 3/1998 | Lam | |
| 5,733,325 A | 3/1998 | Robinson et al. | |
| 5,746,745 A | 5/1998 | Abele et al. | |
| 5,762,631 A | 6/1998 | Klein | |
| 5,772,669 A | 6/1998 | Vrba | |
| 5,776,142 A | 7/1998 | Gunderson | |
| 5,817,102 A | 10/1998 | Johnson et al. | |
| 5,836,965 A | 11/1998 | Jendersee et al. | |
| 5,913,871 A | 6/1999 | Werneth et al. | |
| 5,935,135 A | 8/1999 | Bramfitt et al. | |
| 5,941,908 A | 8/1999 | Goldsteen et al. | |
| 5,944,726 A | 8/1999 | Blaeser et al. | |
| 5,954,729 A | 9/1999 | Bachmann et al. | |
| 5,968,069 A | 10/1999 | Dusbabek et al. | |
| 5,976,155 A | 11/1999 | Foreman et al. | |
| 6,007,543 A | 12/1999 | Ellis et al. | |
| 6,007,545 A | 12/1999 | Venturelli | |
| 6,027,510 A | 2/2000 | Alt | |
| 6,051,001 A | 4/2000 | Borghi | |
| 6,053,943 A | 4/2000 | Edwin et al. | |
| 6,066,169 A | 5/2000 | McGuinness | |
| 6,077,273 A | 6/2000 | Euteneuer et al. | |
| 6,077,295 A | 6/2000 | Limon et al. | |
| 6,077,297 A | 6/2000 | Robinson et al. | |
| 6,106,530 A | 8/2000 | Harada | |
| 6,110,180 A | 8/2000 | Foreman et al. | |
| 6,120,522 A | 9/2000 | Vrba et al. | |
| 6,123,712 A | 9/2000 | Di Caprio et al. | |
| 6,126,685 A | 10/2000 | Lenker et al. | |
| 6,149,996 A | 11/2000 | Helgerson et al. | |
| 6,159,227 A | 12/2000 | Di Caprio et al. | |
| 6,168,616 B1 | 1/2001 | Brown, III | |
| 6,168,617 B1 | 1/2001 | Blaeser et al. | |
| 6,203,558 B1 | 3/2001 | Dusbabek et al. | |
| 6,214,036 B1 | 4/2001 | Letendre et al. | |
| 6,228,110 B1 | 5/2001 | Munsinger | |
| 6,241,738 B1 | 6/2001 | Dereume | |
| 6,254,632 B1 | 7/2001 | Wu et al. | |
| 6,258,099 B1 | 7/2001 | Mareiro et al. | |
| 6,264,683 B1 | 7/2001 | Stack et al. | |
| 6,280,412 B1 | 8/2001 | Pederson, Jr. et al. | |
| 6,296,660 B1 | 10/2001 | Roberts et al. | |
| 6,302,906 B1 | 10/2001 | Goicoechea et al. | |
| 6,309,402 B1 | 10/2001 | Jendersee et al. | |
| 6,322,586 B1 | 11/2001 | Monroe et al. | |
| 6,325,814 B1 | 12/2001 | Euteneuer et al. | |
| 6,331,188 B1 | 12/2001 | Lau et al. | |
| 6,350,277 B1 | 2/2002 | Kocur | |
| 6,371,962 B1 | 4/2002 | Ellis et al. | |
| 6,375,676 B1 | 4/2002 | Cox | |
| 6,380,457 B1 | 4/2002 | Yurek et al. | |
| 6,391,032 B2 | 5/2002 | Blaeser et al. | |
| 6,391,050 B1 | 5/2002 | Broome | |
| 6,391,051 B2 | 5/2002 | Sullivan, III et al. | |
| 6,395,008 B1 | 5/2002 | Ellis et al. | |
| 6,395,017 B1 | 5/2002 | Dwyer et al. | |
| 6,419,685 B2 | 7/2002 | Di Caprio et al. | |
| 6,428,566 B1 | 8/2002 | Holt | |
| 6,443,979 B1 | 9/2002 | Stalker et al. | |
| 6,468,298 B1 | 10/2002 | Pelton | |
| 6,468,299 B2 | 10/2002 | Stack et al. | |
| 6,494,906 B1 | 12/2002 | Owens | |
| 6,506,201 B2 | 1/2003 | Di Caprio et al. | |
| 6,517,547 B1 | 2/2003 | Feeser et al. | |
| 6,517,570 B1 | 2/2003 | Lau et al. | |
| 6,569,192 B1 | 5/2003 | Foreman et al. | |
| 6,582,460 B1 * | 6/2003 | Cryer | A61F 2/95 623/1.11 |
| 6,607,551 B1 | 8/2003 | Sullivan et al. | |
| 6,620,191 B1 | 9/2003 | Svensson | |
| 6,623,518 B2 | 9/2003 | Thompson et al. | |
| 6,660,031 B2 | 12/2003 | Tran et al. | |
| 6,676,667 B2 | 1/2004 | Mareiro et al. | |
| 6,682,553 B1 | 1/2004 | Webler, Jr. | |
| 6,776,791 B1 | 8/2004 | Stallings et al. | |
| 6,814,746 B2 | 11/2004 | Thompson et al. | |
| 6,837,901 B2 | 1/2005 | Rabkin et al. | |
| 6,858,034 B1 * | 2/2005 | Hijlkema | A61F 2/95 606/108 |
| 6,890,337 B2 | 5/2005 | Feeser et al. | |
| 6,896,180 B2 | 5/2005 | Miodunski et al. | |
| 6,960,227 B2 | 11/2005 | Jones et al. | |
| 7,001,422 B2 | 2/2006 | Escamilla et al. | |
| 7,152,605 B2 | 12/2006 | Khairkhahan et al. | |
| 2001/0007082 A1 | 7/2001 | Dusbabek et al. | |
| 2002/0049466 A1 | 4/2002 | Euteneuer et al. | |
| 2002/0055767 A1 | 5/2002 | Forde et al. | |
| 2002/0095204 A1 | 7/2002 | Thompson et al. | |
| 2002/0099435 A1 | 7/2002 | Stinson | |
| 2002/0120321 A1 | 8/2002 | Gunderson et al. | |
| 2002/0120322 A1 | 8/2002 | Thompson et al. | |
| 2002/0120323 A1 | 8/2002 | Thompson et al. | |
| 2002/0123794 A1 | 9/2002 | Ellis et al. | |
| 2002/0138081 A1 | 9/2002 | Blaeser et al. | |
| 2002/0144757 A1 | 10/2002 | Craig et al. | |
| 2002/0151955 A1 | 10/2002 | Tran et al. | |
| 2002/0156519 A1 | 10/2002 | Di Caprio et al. | |
| 2003/0018380 A1 | 1/2003 | Craig et al. | |
| 2003/0077200 A1 | 4/2003 | Craig et al. | |
| 2003/0114912 A1 | 6/2003 | Sequin et al. | |
| 2003/0212451 A1 | 11/2003 | Cox et al. | |
| 2004/0084523 A1 | 5/2004 | Miodunski et al. | |
| 2004/0148008 A1 * | 7/2004 | Goodson, IV | A61F 2/962 623/1.12 |
| 2004/0204749 A1 | 10/2004 | Gunderson | |
| 2005/0131514 A1 | 6/2005 | Hijlkema et al. | |
| 2005/0165439 A1 | 7/2005 | Weber et al. | |
| 2005/0228478 A1 | 10/2005 | Heidner | |

FOREIGN PATENT DOCUMENTS

| | | |
|---|---|---|
| EP | 1369098 A1 | 12/2003 |
| WO | 9322986 A1 | 11/1993 |
| WO | 9415549 A1 | 7/1994 |
| WO | 9807390 A1 | 2/1998 |
| WO | 0071058 A1 | 11/2000 |
| WO | 0232496 A1 | 4/2002 |
| WO | 0241805 A2 | 5/2002 |
| WO | 0247582 A2 | 6/2002 |

OTHER PUBLICATIONS

International Search Report, PCT/US2004/011023, Oct. 11, 2004.
Schetsky, L, "Shape Memory Alloys", Encyclopedia of Chemical Technology (3rd ed.), John Wiley and Sons, vol. 20:726-736, 1982.
International Application No. PCT/US2005/011752 Search report, Aug. 26, 2005.
All non-patent literature documents and foreign patent documents have been previously uploaded in the parent U.S. Appl. No. 11/100,712, filed Apr. 7, 2005.

* cited by examiner

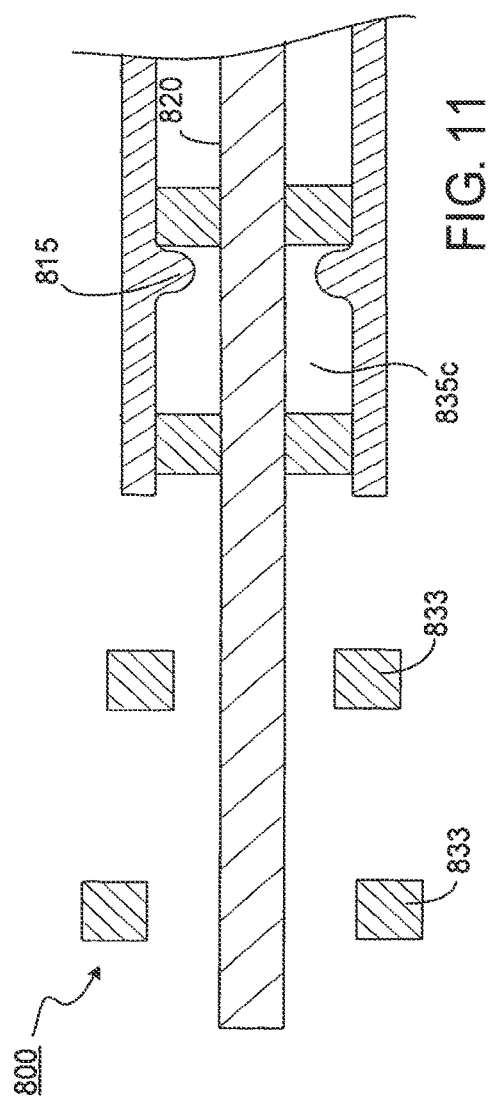
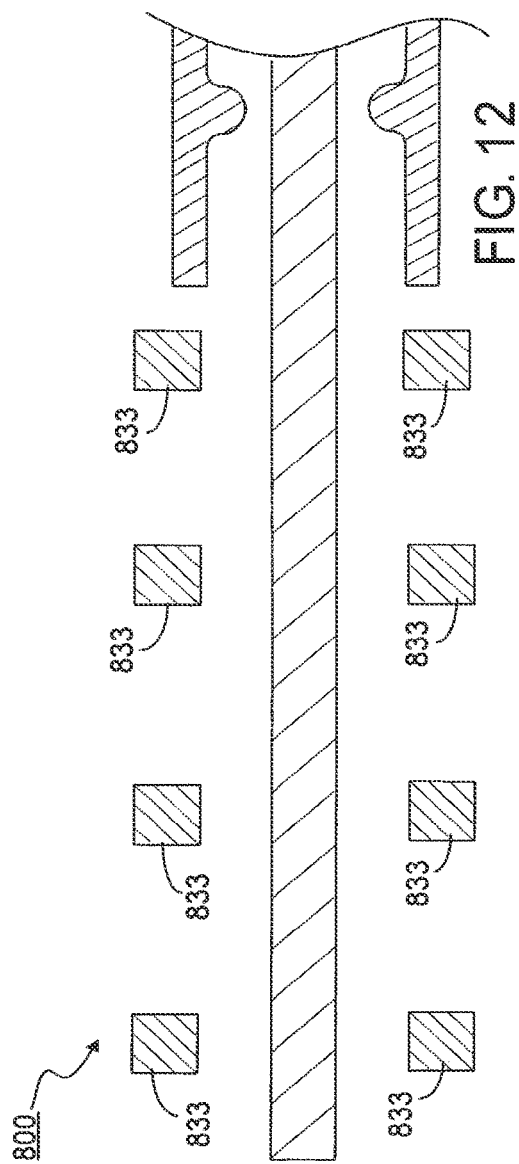

MEDICAL DEVICE DELIVERY SYSTEMS

CROSS-REFERENCE TO RELATED APPLICATIONS

This application is a continuation of co-pending U.S. patent application Ser. No. 11/100,712, filed Apr. 7, 2005, which is a continuation-in-part of, and claims priority under 35 U.S.C. §120 to, co-pending and commonly owned U.S. patent application Ser. No. 10/822,251, filed on Apr. 9, 2004, and entitled "Medical Device Delivery Systems", the entire contents of which are herein incorporated by reference.

TECHNICAL FIELD

This invention relates to medical device delivery systems, and related methods and components.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include a sheath surrounding a catheter with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen. In many instances, a bumper can be included in the system to, for example, aid in deployment of the stent from the system.

SUMMARY

The invention relates to medical device delivery systems, and related methods and components.

In general, the invention relates to implantable medical endoprosthesis delivery systems (e.g., stent delivery systems), as well as related components and methods. The systems can be used, for example, to deliver a medical endoprosthesis (e.g., a stent) to a desired location within a lumen of a subject (e.g., an artery of a human).

In some embodiments, the inner member has a portion that extends outwardly (e.g., a retainer) so that it can be partially disposed over the implantable medical endoprosthesis and so that it can interdigitate with the implantable medical endoprosthesis. In certain embodiments, the outer member has a portion that extends inwardly (e.g., a retainer) so that it can interdigitate with the implantable medical endoprosthesis.

In some embodiments, methods can include at least partially disposing a medical endoprosthesis (e.g., a stent) within a lumen of a subject (e.g., an artery of a human). The methods can include moving the outer member proximally (e.g., so that the implantable medical endoprosthesis is released and can engage a wall of the lumen).

In certain embodiments, an implantable medical endoprosthesis delivery system can exhibit relatively high accuracy in positioning an implantable medical endoprosthesis, and/or increased control over the deployment of an implantable medical endoprosthesis.

In some embodiments, a portion of a medical endoprosthesis delivery system that interdigitates with an implantable medical endoprosthesis delivery system can provide an operator of an implantable medical endoprosthesis delivery system with information about the location of the implantable medical endoprosthesis within the system. As an example, one or more radiopaque materials and/or one or more MRI-visible materials can be used to form the portion of the medical endoprosthesis delivery system that interdigitates with the implantable medical endoprosthesis delivery system.

Features and advantages of the invention are in the description, drawings, and claims.

DESCRIPTION OF DRAWINGS

FIGS. 8-12 are side views of a distal portion of an embodiment of an implantable medical endoprosthesis delivery system at different stages of delivery of the implantable medical endoprosthesis.

DETAILED DESCRIPTION

Figure 1:
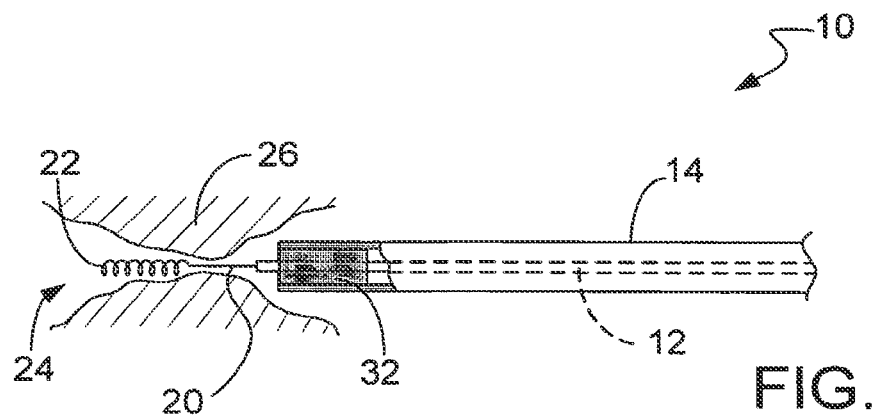
FIGS. 1-3 are side views of a distal portion of an embodiment of an implantable medical endoprosthesis delivery system at different stages of delivery of the implantable medical endoprosthesis.
Figure 2:
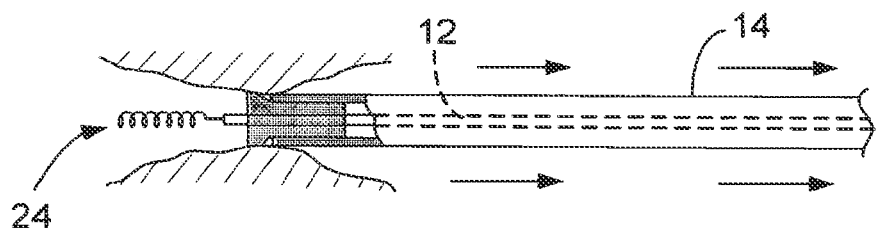
Figure 3:
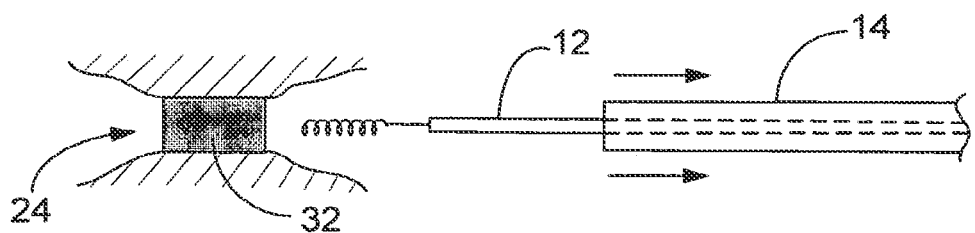

FIGS. 1-3 show a distal end of an implantable medical endoprosthesis delivery system 10 that includes an inner member 12, an outer member 14 surrounding inner member 12, and a stent 32 positioned between inner member 12 and outer member 14. The distal end of system 10 is dimensioned for insertion into a body lumen (e.g., an artery of a human). A guide wire 20 with a blunted end 22 is inserted into a body lumen 24 by, for example, making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. Outer member 14 is moved proximally, allowing stent 32 to expand and engage constricted site 26. Outer member 14, inner member 12 and guide wire 20 are removed from body lumen 24, leaving stent 32 engaged with constricted site 26.

Figure 4:
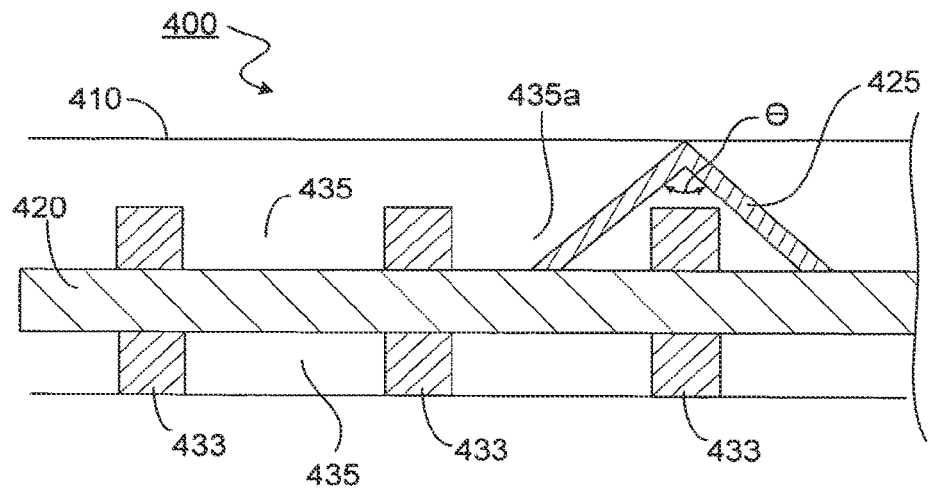
FIGS. 4-7 are side views of a distal portion of an embodiment of an implantable medical endoprosthesis delivery system at different stages of delivery of the implantable medical endoprosthesis.

FIG. 4 shows a stent delivery system 400 that includes an outer member 410, an inner member 420 and a stent having struts 433 and openings 435 between struts 433. Inner member 420 includes a retainer 425 disposed around the outer circumference of inner member 420. Retainer 425 is partially disposed over the stent and interdigitated with an opening 435a in the stent. As explained below with reference to FIGS. 5-7, system 400 can be used to deliver the stent with enhanced accuracy and/or control.

Figure 5:
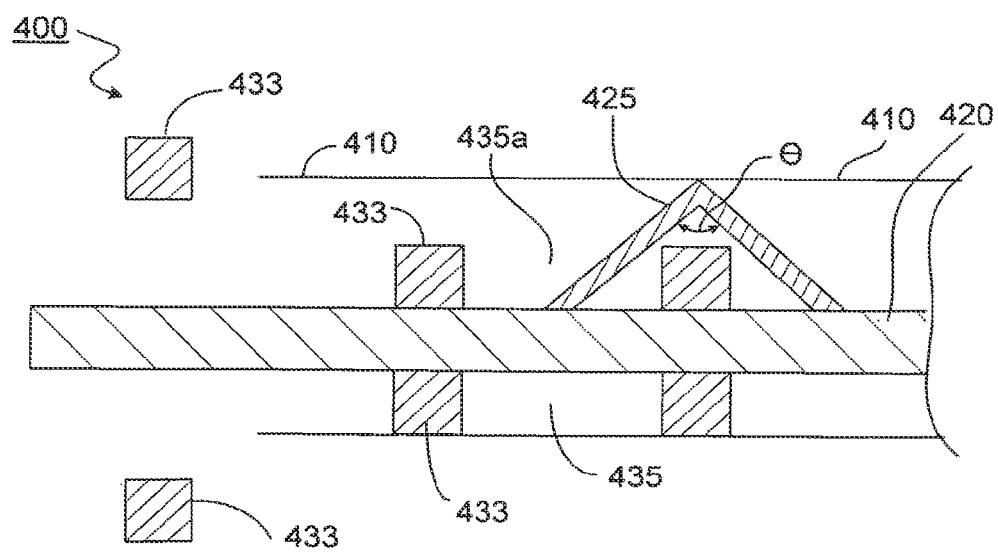
Figure 6:
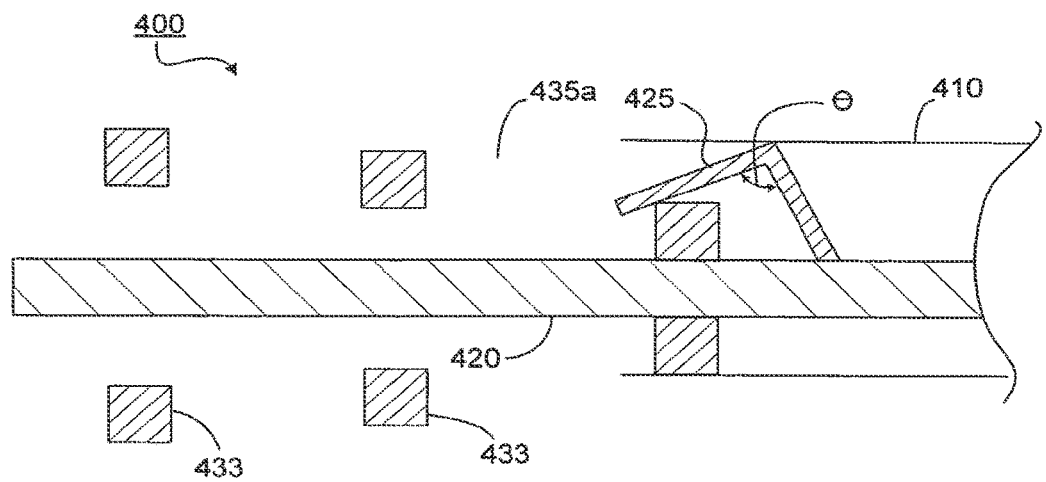
Figure 7:
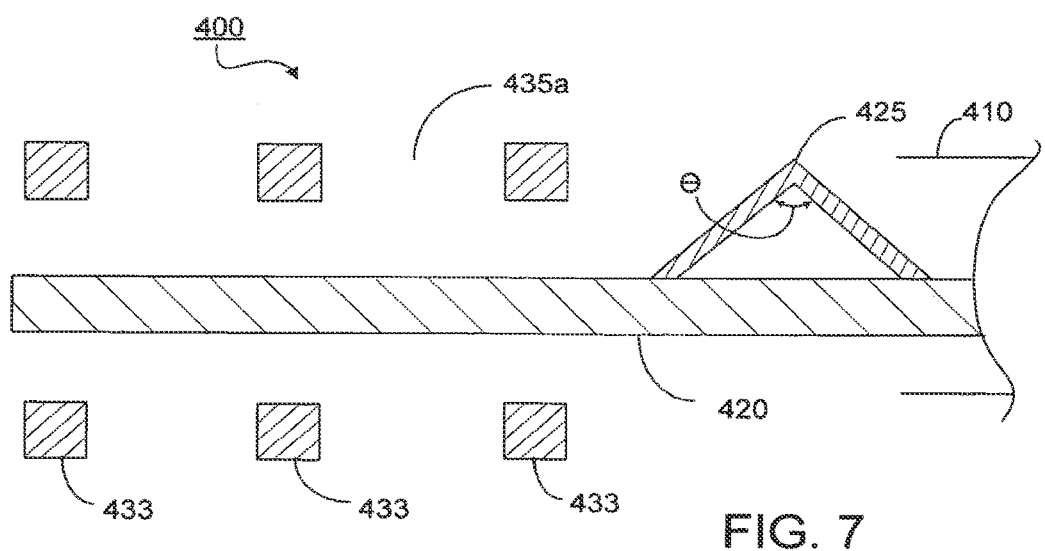

In FIG. 5, outer member 410 has moved proximally an amount sufficient to release a distal portion of the stent, but retainer 425 remains partially disposed over the stent and interdigitated with opening 435a in the stent. In FIG. 6, outer member 410 has moved proximally an amount sufficient to release almost all of the stent. Retainer 425 is no longer interdigitated with opening 435a, but retainer 425 remains partially disposed over the stent. In FIG. 7, outer member 410 has moved proximally of the proximal end of the stent, and the stent is fully released. As shown in FIGS. 5-7, during the stages in the release of the stent, the stent remains substantially unmoved with respect to the distal direction.

In certain embodiments, retainer 425 is designed so that the angle, θ, remains substantially unchanged during release of the stent. This can reduce the amount of potential energy that becomes stored in retainer 425 during the stages in the release of the stent, which can enhance the ability to control the positioning of the stent during its release. In some embodiments, the angle, θ, remains can change during release of the stent (e.g., one or more portions of retainer 425 can distort during release of the stent).

Although shown as being triangular, more generally, retainer 425 can have any desired shape. Examples of shapes that retainer 425 can include U-shaped, square shaped, rectangular shaped and semi-circular shaped.

In general, retainer 425 is formed of a material that is rigid enough for retainer 425 to substantially prevent the stent from moving distally while retainer 425 is interdigitated with the stent, but that is flexible enough to pivot and allow the full release of the stent as outer member 410 is moved proximally over the proximal end of the stent. Examples of materials from which retainer 425 can be formed include polymers, metals, alloys, ceramics and fiber reinforced composites.

Examples of polymers include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), high-density polyethylene (HDPE), low-density polyethylene (LDPE), polyamides (e.g., nylons, Vestamidˆ, polyimides, and combinations of these materials. In certain embodiments (e.g., when it is desirable to reduce the force used to retract outer member 410), retainer 425 can be made of a material having a relatively low coefficient of friction (e.g., a fluoropolymer or a silicone). Examples of fluoropolymers include PTFE and FEP Alternatively or additionally, retainer 425 can be made of a material that includes a lubricious additive (e.g., a fluoropolymer, a silicone, an ultrahigh molecular weight polyethylene, an oil, or blends thereof).

Examples of metals and alloys include stainless steel, platinum, gold, tantalum, MP35N (a nickel-cobalt-chromium-molybdenum alloy), nickel-titanium alloys (e.g., FLEXINOL®, manufactured by Dynalloy, Inc. of Costa Mesa, Calif.) and shape-memory materials. Examples of shape memory materials include metal alloys, such as nitinol (e.g., 55% nickel, 45% titanium), silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). See, e.g., Schetsky, L. McDonald, "Shape Memory Alloys", Encyclopedia of Chemical Technology (3rd ed.), John Wiley & Sons, 1982, vol. 20. pp. 726-736.

In some embodiments, retainer 425 can be entirely or partially formed of one or more radiopaque materials (e.g., to enhance the visibility of retainer 425 during X-ray fluoroscopy). Certain radiopaque materials (e.g., platinum, gold, tantalum) are noted above. Additional radiopaque materials include platinum enriched stainless steels, such as disclosed in published U.S. patent applications US-2003-0018380-A1, 2002-0144757-A1, and 2003-0077200-A1, all of which are hereby incorporated by reference. In certain embodiments in which retainer 425 is partially formed of a radiopaque material, retainer 425 is formed of a polymer having the radiopaque material(s) disposed therein.

In some embodiments, retainer 425 can be entirely or partially formed of one or more MRI-visible materials. As used herein, a MRI-visible material refers to a material that has a magnetic susceptibility of at most about one or less (e.g., at most about 0.5 or less; at most about zero or less) when measured at 25° C. An MRI-visible material can be, for example, a non-ferrous metal-alloy containing paramagnetic elements (e.g., dysprosium or gadolinium) such as terbium-dysprosium, dysprosium, and gadolinium; a non-ferrous metallic band coated with an oxide or a carbide layer of dysprosium or gadolinium (e.g., $Dy_2O_3$ or $Gd_2O_3$); a non-ferrous metal (e.g., copper, silver, platinum, or gold) coated with a layer of superparamagnetic material, such as nanocrystalline $Fe_3C>4$, $CoFe_2C>4$, $MnFe_2O_4$, or $MgFe_2O_4$; or nanocrystalline particles of the transition metal oxides (e.g., oxides of Fe, Co, Ni).

In general, retainer 425 can be integral with inner member 420 or retainer can be a separate element that is attached to inner member 420. In embodiments in which retainer 425 is integral with inner member 420, retainer 425 can be formed, for example, by molding (e.g., extrusion molding, blow molding, injection molding, insert molding), and/or using material removal methods (e.g., lapping, laser removal, water jet removal).

In embodiments in which retainer 425 is attached to inner member 420, retainer 425 and inner member 420 are generally formed separately and subsequently attached, such as, for example, using RF heating, laser bonding, microwave heating, and/or an adhesive. Examples of adhesives include epoxy adhesives, UV curable adhesives and cyanoacrylate adhesive (e,g., medical grade cyanoacrylate adhesives). Commercially available adhesives include epoxy adhesives available from HB Fuller (e.g., HB Fuller 3507 epoxy adhesive, HB Fuller 2139 epoxy adhesive) and the Loctite® brand products available from Henkel Technologies (e.g., Assure™ 425 Surface Curing Threadlocker).

In general, the stent is a self-expanding stent. Examples of materials from which the stent include shape memory materials, such those disclosed above regarding retainer 425.

Inner member 410 and outer member 420 are generally made of polymeric materials, such as those disclosed above regarding retainer 425.

Figure 8:
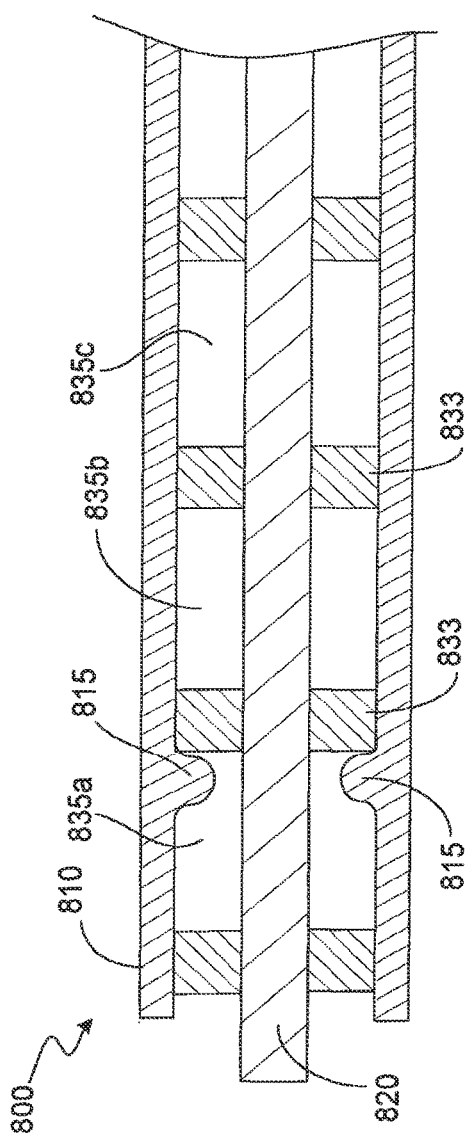

While embodiments have been described in which an inner member has a retainer, in some embodiments, an outer member can have a retainer. For example, FIG. 8 shows a stent delivery system 800 that includes an outer member 810, an inner member 820 and a stent having struts 833 and openings 835 between openings 835. Outer member 810 includes a retainer 815 disposed around the inner circumference of outer member 810. Retainer 815 is interdigitated with an opening 835a in the stent. As explained below with reference to FIGS. 9-12, system 800 can be used to deliver the stent with enhanced accuracy and/or control.

Figure 9:
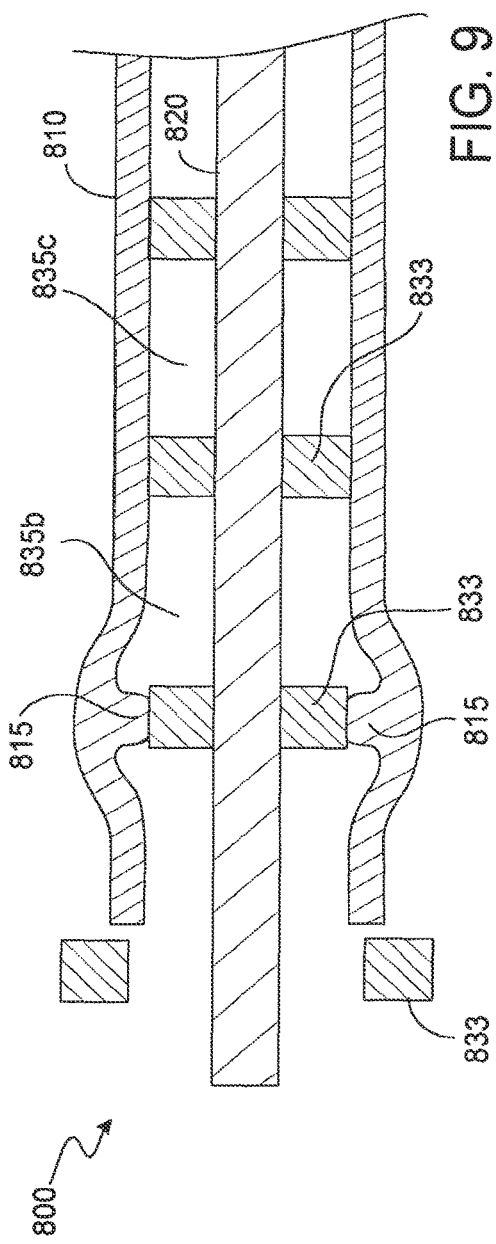
Figure 10:
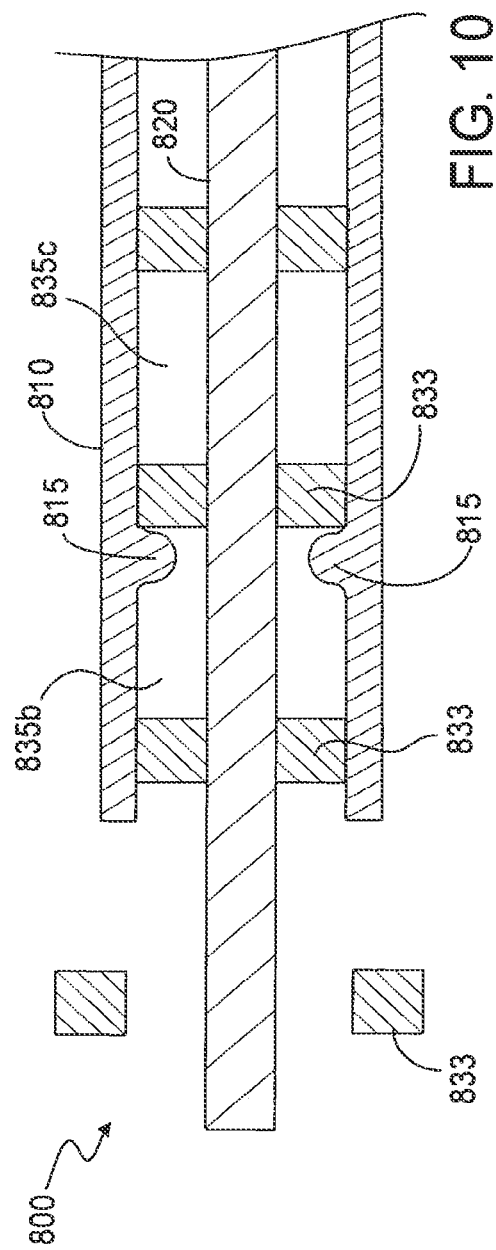

In FIG. 9, outer member 810 has moved proximally so that a portion of outer member 810 is distorted outwardly and so that retainer 815 is on a strut 833. In FIG. 10, outer member 810 has moved proximally an amount sufficient to release a distal portion of the stent, but retainer 815 has also moved proximally and is now interdigitated with an opening 835b (located proximally of opening 835a) of the stent. In FIG. 11, outer member 810 has moved proximally an amount sufficient to release most of the stent, but retainer 815 has also moved more proximally and is now interdigitated with an opening 835c (located proximally of opening 835a and 835b) of the stent. In FIG. 12, outer member 810 has moved proximally of the proximal end of the stent, and the stent is fully released. As shown in FIGS. 9-12, during the stages in the release of the stent, the stent remains substantially unmoved with respect to the distal direction.

Generally, retainer 815 is designed so that it can move relatively smooth over the stent as outer member 810 is moved proximally. This can reduce the amount of potential energy that becomes stored in retainer 815 during the stages in the release of the stent, which can enhance the ability to control the positioning of the stent during its release.

In general, retainer 815 can be formed of one or more of the materials disclosed above regarding retainer 425.

Generally, retainer 815 can be integral with outer member 810 or retainer can be a separate element that is attached to outer member 810. In general, retainer 815 can be formed using the methods disclosed above regarding retainer 425.

While certain embodiments of an outer member having a retainer have been described, other embodiments are possible. As an example, the retainer could be formed of an inflatable member (e.g., an inflatable balloon) that extends inwardly from the outer member. The size and shape of the inflatable member could be manipulated by inflating or deflating the inflatable member. As an example, the inflatable member could be configured so that, the inflatable member extends inwardly from the outer member and acts as a retainer when inflated, but extends inwardly little if any distance and does not act as a retainer when deflated. As another example, the inflatable member could be configured to interdigitate with multiple struts of a stent when inflated, and interdigitate with fewer (e.g., none) of the struts when deflated.

While certain embodiments have been described, other embodiments are possible. As an example, while embodiments have been described in which a retainer is disposed around the outer circumference of an inner member, in some embodiments a retainer can be disposed around only a portion of the outer circumference of the inner member.

As another example, while embodiments have been described in which a retainer is disposed around the inner circumference of an outer member, in some embodiments a retainer can be disposed around only a portion of the inner circumference of the outer member. As a further example, in some embodiments, an inner member can include multiple retainers. The retainers can be positioned radially around the inner member (e.g., at substantially the same distance longitudinally along the inner member), and/or the retainers can be positioned at different distances longitudinally along the inner member.

As another example, while embodiments have been described in which an outer member includes a single retainer, in some embodiments, an outer member can include multiple retainers. The retainers can be positioned radially around the outer member (e.g., at substantially the same distance longitudinally along the outer member), and/or the retainers can be positioned at different distances longitudinally along the outer member.

As a further example, while embodiments have been described in which an inner member has one or more retainers or an outer member has one or more retainers, in some embodiments, each of the inner and outer members can have one or more retainers.

As an additional example, while the retention of self-expanding stents has been described, other types of implantable medical endoprostheses are capable of being retained by a retainer. Examples of implantable medical endoprostheses include balloon-expandable stents, stent-grafts and vena cava filters.

As another example, in some embodiments, a retainer (e.g., a retainer on an inner member, a retainer on an outer member) can be formed of a material that changes shape so that, without moving the inner or outer members, the retainer is interdigitated with the stent when the retainer has one shape, and the retainer is not interdigitated with the stent when the retainer has another shape. For example, the retainer can be formed of an electroactive polymer that changes shape when a current is applied to the material. In such embodiments, the retainer could be configured to interdigitate with the stent when an electric current is not applied to the material, and the retainer could be configured to not interdigitate with the stent when a current is applied to the material, or vice-versa.

Other embodiments are in the claims.

What is claimed is:

1. A stent delivery system, comprising:
   an inner member;
   wherein a stent receiving region is defined along the inner member;
   a deployment sheath slidably disposed along the inner member; and
   a stent holding member pivotably coupled to the inner member at a position proximal of the stent receiving region, the stent holding member being designed to shift between a first configuration where a distal end of the stent holding member contacts the inner member and a second configuration where the distal end of the stent holding member is radially spaced from the inner member, and wherein the stent holding member is in the first configuration when the stent holding member is not covered by the deployment sheath and wherein the distal end of the stent holding member is closer to the inner member when in the first configuration than when in the second configuration.

2. The stent delivery system of claim 1, wherein the stent holding member includes an outwardly extending region and an angled region.

3. The stent delivery system of claim 2, wherein the angled region has an angle that remains constant when the stent holding member shifts between the first configuration and the second configuration.

4. The stent delivery system of claim 1, wherein the stent holding member is in the first configuration when the deployment sheath is positioned about the stent holding member.

5. The stent delivery system of claim 1, wherein the stent holding member shifts to the second configuration when the deployment sheath is retracted to a position proximal of the distal end of the stent holding member.

6. The stent delivery system of claim 1, further comprising a stent disposed along the stent receiving region.

7. The stent delivery system of claim 6, wherein the distal end of the stent holding member is designed to interdigitate with the stent.

8. The stent delivery system of claim 6, wherein the stent is a self-expanding stent.

9. A stent delivery system, comprising:
   an inner member;

wherein a stent receiving region is defined along the inner member;

a deployment sheath slidably disposed along the inner member;

a stent retainer pivotably disposed adjacent to the stent receiving region, the stent retainer having an outwardly extending region, an angled region, and a distal end designed to be positioned distally of a proximal end of a stent disposed along the stent receiving region; and wherein the stent retainer is designed to shift between a first configuration and a second configuration, wherein when the stent retainer is in the first configuration the angled region is disposed radially outward of an outer surface of the stent and where the distal end of the stent retainer contacts the inner member, wherein when the stent retainer is in second configuration the distal end of the stent retainer is radially spaced from the inner member, wherein the stent retainer is in the first configuration when the stent retainer is not covered by the deployment sheath, and wherein the distal end of the stent retainer is closer to the inner member when in the first configuration than when in the second configuration.

10. The stent delivery system of claim 9, wherein the angled region has an angle that remains constant when the stent retainer shifts between the first configuration and the second configuration.

11. The stent delivery system of claim 9, wherein the stent retainer is in the first configuration when the deployment sheath is positioned about the stent retainer.

12. The stent delivery system of claim 9, wherein the stent retainer shifts to the second configuration when the deployment sheath is retracted to a position proximal of the distal end of the stent retainer.

13. The stent delivery system of claim 9, wherein the distal end of the stent retainer is designed to interdigitate with the stent.

14. A stent delivery system, comprising:
an inner member;
wherein a stent receiving region is defined along the inner member;

a self-expanding stent disposed along the stent receiving region;

a deployment sheath slidably disposed along the inner member;

a stent retainer pivotably disposed adjacent to the stent receiving region, the stent retainer having an outwardly extending region, an angled region, and a distal end designed to be positioned distally of a proximal end of the stent;

wherein the stent retainer is designed to shift between a first configuration and a second configuration, wherein when the stent retainer is in the first configuration the angled region is disposed radially outward of an outer surface of the stent and where the distal end of the stent retainer contacts the inner member, wherein when the stent retainer is in second configuration the distal end of the stent retainer is radially spaced from the inner member, wherein the stent retainer is in the first configuration when the stent retainer is not covered by the deployment sheath, and wherein the distal end of the stent retainer is closer to the inner member when in the first configuration than when in the second configuration; and wherein the angled region has an angle that remains constant when the stent retainer shifts between the first configuration and the second configuration.

15. The stent delivery system of claim 14, wherein the stent retainer is in the first configuration when the deployment sheath is positioned about the stent retainer.

16. The stent delivery system of claim 14, wherein the stent retainer shifts to the second configuration when the deployment sheath is retracted to a position proximal of the distal end of the stent retainer.

17. The stent delivery system of claim 14, wherein the distal end of the stent retainer is designed to interdigitate with the stent.

* * * * *